United States Patent [19]

Stolar

[11] 4,041,160

[45] Aug. 9, 1977

[54] WATER-SUSPENDIBLE COMPOSITION COMPRISING ROBENIDINE

[75] Inventor: Morris E. Stolar, Tel-Aviv, Israel

[73] Assignee: Abic Ltd., Israel

[21] Appl. No.: 645,379

[22] Filed: Dec. 30, 1975

[30] Foreign Application Priority Data

Jan. 8, 1975   Israel .................................... 46406

[51] Int. Cl.$^2$ ................... A61K 31/63; A61K 31/635; A61K 31/155

[52] U.S. Cl. .................................. 424/229; 424/228; 424/326

[58] Field of Search ................ 424/326, 228, 229

[56] References Cited

U.S. PATENT DOCUMENTS

| | | | |
|---|---|---|---|
| 2,904,469 | 9/1959 | Nashed | 424/80 |
| 3,901,944 | 8/1975 | Tomcufcik | 424/326 |

OTHER PUBLICATIONS

Koninklijke–Chem. Abst., vol. 55 (1961) p. 19150c.

*Primary Examiner*—Sam Rosen
*Attorney, Agent, or Firm*—Steinberg & Blake

[57] ABSTRACT

There are disclosed water-suspendable compositions comprising a 1,3-bis-[(p-chlorobenzylidene)-amino]-guanidine (called Robenidine) or one of its salts. Said compositions comprise also N-methyl-2-pyrrolidone, a protective colloid water and, if required, a buffer yielding to the composition a pH of 7–9.5. Said composition may comprise additional substances, e.g., a potentiated or unpotentiated sulfa drug. There are also disclosed aqueous suspensions comprising the above composition and a method for the treatment of animals being infected with Cocciodiosis with said aqueous suspension.

15 Claims, No Drawings

WATER-SUSPENDIBLE COMPOSITION COMPRISING ROBENIDINE

The present invention relates to a water-suspendable composition comprising 1.3-bis-[(-p-chlorobenzylidene)-amino guanidine (hereinafter called "Robenidine") or one of its salts. The present invention will be in particular illustrated with reference to Robenidine hydrochloride but is not restricted thereto.

It is shown that Robenidine hydrochloride can be utilised in the treatment of warm blooded animals, in particular fowl, infected with the protozoal disease Coccidiosis. See, for example, W. M. Reich et al, Avian diseases 14 (4) 142, (1971); S. Kantor et al, Science 168, 375–4 (1970); British Patent Specification No. 1,256,723; J. F. Ryley and R. G. Wilson, Z. Parazitenk 37, 85–93 (1971).

A veterinary medicine which has to be administered in a dose which is as uniform as possible admixed either with the food or with the drinking water. The preferred manner of administration is as part of the drinking water for the following reasons: The administration of medicated feed to animals which are sick is often unsatisfactory. In this state of health, the appetite of the animals is reduced, so that they swallow a lower amount of feed and as the result thereof take in a dose of the medicine which is less than the therapeutically required one. On the other hand animals which are sick usually continue drinking water.

Moreover, it is known that warm-blooded animals drink about twice the amount that they eat and thus about half the concentration of the drug required in the feed is required in water. In addition, the presence of a drug in a solution enhances curing because of better availability. Finally, the administration of a veterinary medicine for curing purposes in an aqueous solution or suspension has the advantage of being simpler and more convenient than the administration as part of the feed. In the first case the farmer or the veterinarian obtains a composition comprising the active material which composition can be readily mixed with water, while if he administers a medicated feed he is dependent on the supply from the feed manufacturer.

French Patent Specification No. 2,012,054 states that the various Robenidine salts are very soluble in water and hints that said salts can be administered as part of the drinking water.

The therapeutically effective dose of Robenidine salts varies from animal to animal. Thus, for example, the recommended does for fowl in feed is 30 mg per kg feed. It has now been found by the applicants that for a complete cure about 15 mg per L of drinking water is sufficient in the treatment of fowl.

Applicants have tried to establish the solubility and/or suspendability of some Robenidene salts in water at room temperature. They have found that after about ½ hour only 5 mg of the hydrochloride or of the nitrate were dissolved in 1 L of water. (Of the sulfate and the hydrobromide no traces could be found after ½ hour of stirring.) Even after constant stirring for about 24 hours only about 8 mg of the hydrochloride or of the nitrate were dissolved in 1 L. of water.

The above rate of solubility is certainly not sufficient for the administration of the Robenidine salt as part of the drinking water. The amount dissolved in water, even after 24 hours is much below the therapeutic dose required. Moreover, in order that a drug may be administered as part of the drinking water it has to be instantaneously soluble or suspendable in water.

In co-pending application Ser. No. 488,476, now U.S. Pat. No. 3,954,996 there is described and claimed a water-soluble composition comprising a Robenidine salt, a suitable water-soluble organic solvent and a suitable water-solubilizer; the solvent and the solubilizer being miscible with each other.

Said composition has certain advantages. However, it has been found that the organic solvents which are utilized are quite expensive. Therefore, the compositions obtained are also quite expensive which sometimes causes their use to be uneconomical.

It is thus desirable to provide a composition comprising Robenidine which would overcome the above drawback, i.e., which would be cheaper in that the amount of the expensive organic solvent required can be reduced.

It has now been found that in order to achieve the desired effect, namely that the Robenidine may be administered as part of the drinking water, the composition need not be completely soluble in water. It is sufficient that upon the addition of the composition to water a suspension is obtained which remains stable for at least 4 hours.

The present invention thus consists in a water-suspendable composition comprising Robenidine or one of its physiologically acceptable salts, N-methyl-2-pyrrolidone, a protective colloid, water and, if required, a buffer which provides the composition with a pH of 7–9.5.

The composition according to the present invention may comprise also additional compounds, in particular such which have a therapeutic effect which may add to or enhance the therapeutic value of said composition.

Thus, for example, it is known that the consumption of excessive amounts of Robenidine tends to impart an undersirable flavor to the meat of animals treated therewith. It has now been found that the coadministraton of a potentiated or unpotentiated sulfa drug together with the Robenidine may be desirable to order to decrease the amount of Robenidine required for therapeutic treatment or to increase the therapeutic effectiveness of Robenidine without dosage increase.

As suitable sulfa drugs there may be mentioned, for example, sulfadiazine, sulfadoxine, sulfadimethoxine, sulfamethoxasol, sulfadimidine and sulfaquinaxoline.

As suitable potentiators there should be mentioned, inter alia, 2,4-diaminopyrimidines carrying a substituted benzyl group in the 5-position; or a substituted phenyl group in the 5-position together with a lower alkyl group in the 6-position. Suitable components of the above class are, for example, trimethoprim, diaveridine, 2,4-diamino-5-(4-chlorobenzyl)-6-ethylpyrimidine; ormethoprim, 2,4-diamino-5-(3,4-dimethoxy-5-bromobenzyl)-pyrimidine and pyrimethamine.

All compounds which are part of the composition according to the present invention, i.e. the colloids, the buffering substances and any further additional compounds, if present, should not be toxic should, be physiologically acceptable, palatable and stable. Naturally they should aid the object of the present invention, i.e. enable the preparation of a stable composition which upon addition of water yields a stable suspension.

A protective colloid is a colloid which is able to prevent the precipitation of another colloid. (See, The American Illustrated Medical Dictionary, Dorland, 22nd Edition, W.B. Saunders Comp., page, 334).

As protective colloids there may be utilized, for example, various gums, e.g., Acacia, PVP, CMC, Methyl Cellulose, Alginates, Xanthan, etc. The preferred colloid is hydroxy-propyl cellulose ether such as Klucel LF (trade Mark of Hercules, Inc., Wilmington, Del.).

As buffer there may be utilized, for example, a suitable phosphate buffer, a NaOH solution, etc.

The ratio of the various ingredients may be varied to a great extent. The preferred compositions comprise 0.02–15% (all percentages are by weight) of Robenidine (calculated as base), 0.03–20% N-methyl-2-pyrrolidone and 1–10% of colloid, the remainder being water and, if required, buffer. The ratio Robenidine:N-methyl-2-pyrrolidone is preferably at least 1:4.6.

The compositions according to the present invention are stable for several months and can be stored for said period.

The compositions according to the present invention can be prepared by mixing processes known per se. However, preferably the composition is prepared as follows:-

The Robenidine or its salt is dissolved in the N-methyl-2-pyrrolidone, if required, with heating, Said solution is then added with stirring to a freshly prepared mixture of the protective colloid and water. The suspension obtained is stirred for some minutes, e.g., about 10 minutes. Thereafter, if required, additional water and the buffer are added with stirring. The composition obtained may then be packed and stored.

The compositions according to the present invention may be used to prepare aqueous suspensions containing a therapeutically effective dose of Robenidine. Said suspensions are obtained instantaneously.

The present invention thus consists also in an aqueous suspension of the composition according to the present invention comprising a therapeutically effective dose of Robenidine or one of its salts.

The therpeutically effective dose of R obenidine varies according to the animals to be treated therewith. However, in the recommended applications said dose should vary between 10–100 mg/1 L of water.

The suspensions obtained are stable for at least 4 hours, i.e., no sedimentation was observed during this period.

The present invention relates also to a method for the treatment of animals, e.g., those being infected with Cocciodiosis, in which said animals drink an aqueous suspension of the composition according to the present invention comprising a therapeutically effective dose of Robenidine or one of its salts.

The present invention will now be illustrated with reference to the follow Examples without being limited by the same.

EXAMPLE 1

A composition was prepared as follows:
a. 0.256 g of Robenidine HCl was dissolved with gentle heating 3 g of N-methyl-2-pyrrolidone.
b. 5 g of Klucel LF were dispersed with stirring in 70 cc of boiling water. The dispersion was then allowed to cool to room temperature.
c. The Robenidine solution was gradually added with stirring to the Klucel LF dispersion. Stirring was continued for about 10 minutes.
d.
The pH was adjusted to 7 by the addition of a NaOH 10% solution and water was added to bring up the volume to 100 cc.

A stable composition was obtained.

In case said composition is to be used in a proportion pump, 7.8 ml of its are diluted with 999.2 ml of water yielding a concentration of 20 ml Robenidine/1 L of water.

However, any desired suspensions comprising about 10–100 mg of Robenidine/1 L of water may be prepared.

The suspensions obtained were stable for at least 4 hours.

EXAMPLE 2

In the same manner as described in Example 1 the following composition was prepared:

| | |
|---|---|
| Robenidine HCl | 0.256 g |
| N-methyl-2-pyrrolidone | 1.400 g |
| Klucel LF | 7.000 g |
| NaOH 10% solution to pH 7 | |
| Water q.s. | 100.000 ml |

The composition obtained was stable.
Suspensions as in Example 1 were prepared, which had also the required stability.

EXAMPLE 3

In the same manner as described in Example 1 the following composition was prepared:

| | |
|---|---|
| Robenidine HCl | 0.020 g |
| N-methyl-2-pyrrolidone | 0.100 g |
| Klucel LF | 4.000 g |
| Phosphate buffer pH 7 q.s. | 100.000 ml |

The composition obtained was stable.
Suspension as in Example 1 were prepared, which had also the required stability.

EXAMPLE 4

In the same manner as described in Example 1 the following composition was prepared:

| | |
|---|---|
| Robenidine nitrate | 10.00 g |
| N-methyl-2-pyrrolidone | 50.00 g |
| NaOH 10% solution to pH 7 | |
| Klucel LF | 5.00 g |
| Water q.s. | 100.00 ml |

The composition obtained was stable.
Suspensions as in Example 1 were prepared, which had also the required stability.

Example 5

In the same manner as described in Example 1 the following composition was prepared:

| | |
|---|---|
| Robenidine HCl | 0.256 g |
| Sulfadimidine | 3.077 g |
| Pyrimethamine | 0.307 g |
| N-methyl-2-pyrrolidone | 5.00 g |
| Klucel LF | 7.00 g |
| Phosphate buffer pH 7 q.s. | 100.00 ml |

The sulfamidine and the pyrimethamine were added in step (a) according to Example 1.
The composition obtained was stable.
7.8 ml of the above suspension were diluted with 992.2 ml of water. A stable composition comprising:

| | |
|---|---|
| Robenidine HCl | 0.020 g |
| Sulfadimidine | 0.240 g |
| Pyrimethamine | 0.024 g | is obtained.

I claim:

1. A composition which forms a stable suspension in water, said composition comprising a compound selected from the group consisting of 1,3-bis-[(p-chlorobenzylidene) amino]-guanidine and physiologically acceptable salts thereof, N-methyl-2-pyrrolidone, a protective colloid and water, buffered to a pH of 7-9.5.

2. A water-suspendible composition according to claim 1 wherein the protective colloid is selected from the group consisting of Acacia, PVP, CMC, Methyl Cellulose, Alginates and Xanthan.

3. A water-suspendible composition according to claim 1 wherein the protective colloid is a hydroxylpropyl cellulose ether.

4. Composition according to claim 1 wherein the ratio of said compound to N-methyl-2-pyrrolidone is at least 1:4.6.

5. Composition according to claim 1 which comprises 0.02-15% of said compound calculated as the base.

6. Composition according to claim 5 which comprises 0.03-20% of N-methyl-2-pyrrolidone.

7. Composition according to claim 6 which comprises 1-10% of protective colloid.

8. Composition according to claim 1, and also including a sulfa drug.

9. Composition according to claim 8 wherein the sulfa drug is selected from the group consisting of sulfadiazine, sulfadoxine, sulfadimethoxine, sulfamethoxasol, sulfadimidine and sulfaquinaxoline.

10. A process for the preparation of a water-suspendible composition according to claim 1 which comprises dissolving said compound in N-methyl-2-pyrrolidone, adding the thus obtained solution to a freshly prepared mixture of the protective colloid and water and buffering the obtained suspension.

11. A process according to claim 10 wherein a sulfa drug is dissolved together with said compound in the N-methyl-2-pyrrolidone.

12. A process according to claim 11, wherein a potentiator is dissolved together with the sulfa drug and the compound in the N-methyl-2-pyrrolidine.

13. An aqueous suspension comprising a composition according to claim 1 containing a therapeutically effective dose of said compound.

14. An aqueous suspension according to claim 1 containing said compound in an amount of 10-100 mg/1 L of water.

15. A method for the treatment of animals wherein an aqueous suspension according to claim 13 is administered to an animal requiring said compound.

* * * * *